US00PP29441P3

(12) United States Plant Patent
Meulenbroek

(10) Patent No.: US PP29,441 P3
(45) Date of Patent: Jul. 3, 2018

(54) STRAWBERRY PLANT NAMED 'OPERA'

(50) Latin Name: *Fragaria×ananassa*
Varietal Denomination: Opera

(71) Applicant: Egbertus Joseph Meulenbroek, Zetten (NL)

(72) Inventor: Egbertus Joseph Meulenbroek, Zetten (NL)

(73) Assignee: FRESH FORWARD HOLDING B.V., Eck en Wiel (NL)

( * ) Notice: Subject to any disclaimer, the term of this patent is extended or adjusted under 35 U.S.C. 154(b) by 0 days.

(21) Appl. No.: 14/999,466

(22) Filed: May 11, 2016

(65) Prior Publication Data

US 2017/0332532 P1 Nov. 16, 2017

(51) Int. Cl.
*A01H 5/08* (2018.01)

(52) U.S. Cl.
USPC ..... Plt./208
CPC ..... *A01H 5/0893* (2013.01)

(58) Field of Classification Search
USPC ..... Plt./208, 209
See application file for complete search history.

(56) References Cited

PUBLICATIONS

UPOV hit on strawberry plant named 'Opera', QZ PBR 20140200, application date Jan. 27, 2014.*

* cited by examiner

*Primary Examiner* — Anne Marie Grunberg
(74) *Attorney, Agent, or Firm* — C. A. Whealy

(57) ABSTRACT

A new and distinct cultivar of Strawberry plant named 'Opera', characterized by its compact and semi-upright plant habit; moderately vigorous to vigorous growth habit; uniform fruit ripening; large broadly rounded to conical fruits that are glossy and red in color; pleasant fruit aroma and taste; excellent fruit postharvest longevity; and moderately resistant to *Verticillium dahliae* and *Phytophthora cactorum*.

6 Drawing Sheets

Botanical designation: *Fragaria×ananassa*.
Cultivar denomination: 'OPERA'.

BACKGROUND OF THE INVENTION

The present Invention relates to a new and distinct cultivar of Strawberry plant, botanically known as *Fragaria×ananassa* and hereinafter referred to by the name 'Opera'.

The new Strawberry plant is a product of a planned breeding program conducted by the Inventor in Elst, Gelderland, The Netherlands. The objective of the breeding program was to develop new early-ripening Strawberry plants with good fruit quality, ease of harvesting, good postharvest longevity and resistance to pathogens.

The new Strawberry plant originated from a cross-pollination by the Inventor during the spring of 2004 in Elst, Gelderland, The Netherlands of a proprietary selection of *Fragaria×ananassa* identified as code name E1998-142, not patented, as the female, or seed, parent with an unnamed seedling selection of *Fragaria×ananassa*, not patented, as the male, or pollen, parent. The new Strawberry plant was discovered and selected by the Inventor as a single plant from within the progeny of the stated cross-pollination in a controlled environment in Elst, Gelderland, The Netherlands during the summer of 2006.

Asexual reproduction of the new Strawberry plant by runner cuttings in a controlled environment at Elst, Gelderland, The Netherlands since the autumn of 2006, has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Opera'. These characteristics in combination distinguish 'Opera' as a new and distinct Strawberry plant:

1. Compact and semi-upright plant habit.
2. Moderately vigorous to vigorous growth habit.
3. Uniform fruit ripening.
4. Large broadly rounded to conical fruits that are glossy and red in color.
5. Pleasant fruit aroma and taste.
6. Excellent fruit postharvest longevity.
7. Moderately resistant to *Verticillium dahliae* and *Phytophthora cactorum*.

Plants of the new Strawberry differ primarily from plants of the female parent selection in the following characteristics:

1. Plants of the new Strawberry are more upright and not as globose as plants of the female parent selection.
2. Plants of the new Strawberry have darker green-colored leaves than plants of the female parent selection.
3. Fruits of plants of the new Strawberry are broadly rounded to conical in shape whereas fruits of plants of the female parent selection are conical in shape.

Plants of the new Strawberry differ primarily from plants of the male parent selection in fruit size as plants of the new Strawberry produce much larger fruits than plants of the male parent selection.

Plants of the new Strawberry can be compared to plants of *Fragaria* L. 'Sonata', disclosed in U.S. Plant Pat. No. 18,000. In side-by-side comparisons, plants of the new Strawberry differ primarily from plants of 'Sonata' in the following characteristics:

1. Plants of the new Strawberry are larger than plants of 'Sonata'.
2. Plants of the new Strawberry are more upright than and not as globose than plants of 'Sonata'.
3. Plants of the new Strawberry have larger leaves with longer petioles than plants of 'Sonata'.
4. Plants of the new Strawberry have larger flowers with larger petals than plants of 'Sonata'.
5. Fruits of plants of the new Strawberry are heavier and darker red in color than fruits of plants of 'Sonata'.
6. Fruits of plants of the new Strawberry are firmer than fruits of plants of 'Sonata'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a side perspective view of a typical flowering and fruiting plant of 'Opera' grown in a container.

The photograph on the second sheet is a close-up view of a typical fully opened flower of 'Opera'.

The photograph on the third sheet is a close-up view of typical developed fruits of 'Opera'.

The photograph on the fourth sheet is a close-up view of the upper surface of typical leaves of 'Opera'.

The photograph on the fifth sheet is a close-up view of the lower surface of a typical fully opened flower of 'Opera'.

The photograph on the sixth sheet comprises longitudinal cross-sectional views of typical fruits of 'Opera'.

DETAILED BOTANICAL DESCRIPTION

The aforementioned photographs, following observations and measurements describe plants grown in 2.5-liter containers during the spring and summer in a glass-covered greenhouse in Elst, Gelderland, The Netherlands and under cultural practices typical of commercial Strawberry production. During the production of the plants, day temperatures ranged from 15° C. to 25° C. and night temperatures ranged from 7° C. to 14° C. Plants were one year old when the photographs and description were taken. In the following description, color references are made to The Royal Horticultural Society Colour Chart, 2001 Edition, except where general terms of ordinary dictionary significance are used.

Botanical classification: *Fragaria×ananassa* 'Opera'.

Parentage:

*Female, or seed, parent*.—Proprietary seedling selection of *Fragaria×ananassa* identified as code name E1998-124, not patented.

*Male, or pollen, parent*.—Unnamed seedling selection of *Fragaria×ananassa*, not patented.

Propagation:

*Type*.—By runner cuttings.

*Time to initiate roots, summer*.—About one to four days at soil temperatures about 15° C.

*Time to produce a rooted young plant, summer*.—About two weeks at soil temperatures ranging from 18° to 20° C.

*Root description*.—Medium in thickness, fibrous; typically cream white to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; compact and semi-upright plant habit; leaves basal; moderately vigorous to vigorous growth habit; moderate growth rate; moderately densely foliated and bushy to somewhat open canopy.

*Plant height*.—About 25 to 35 cm.

*Plant diameter*.—About 40 to 55 cm.

*Stolon texture*.—Sparsely pubescent.

*Stolon color and texture*.—Close to 145A occasionally tinged with close to 185A.

Leaf description:

*Arrangement and appearance*.—Basal rosette; compound with typically three or four leaflets per leaf; relatively large non-variegated leaves.

*Leaflet length*.—About 10 to 13.5 cm.

*Leaflet width*.—About 11 to 13.5 cm.

*Leaflet shape*.—Broadly ovate; terminal leaflet, concave.

*Leaflet apex*.—Obtuse to acute.

*Leaflet base*.—Obtuse to rounded.

*Leaflet margin*.—Serrate to lobed.

*Leaflet texture and luster, upper surface*.—Pubescent; weakly blistered; moderately glossy.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Stipule color*.—Close to 137B occasionally tinged with close to 185A.

*Petioles*.—Length: About 20 to 35 cm. Diameter: About 2.5 to 6 mm. Texture, upper and lower surfaces: Pubescent; attitude of hairs, outwardly to horizontal. Color, upper and lower surfaces: Close to 145A.

Flower description:

*Flower form and flowering habit*.—Rotate flowers arranged singly at lateral apices; flowers held at the foliar plane; about 30 to 50 flowers developing per plant; flowers are self-fertile.

*Fragrance*.—None detected.

*Natural flowering season*.—Plants flower in late April to early May in The Netherlands, considered early to midseason.

*Flower diameter*.—About 2.5 to 3.5 cm.

*Flower depth (height)*.—About 6 mm to 11 mm.

*Petals*.—Arrangement: Single whorl of five or six petals; petals not imbricate. Length: About 1 cm to 1.3 cm. Width: About 1 cm to 1.4 cm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of 10 to 16 sepals; calyx, star-shaped; calyx adherence is weak to moderate; sepal attachment is initially inserted with primary and secondary fruits and becoming more level with subsequent fruit production; sepals are orientated upwards from the fruit. Calyx diameter: About 1 cm to 2.5 cm. Length: About 1 cm to 2 cm. Width: About 5 mm to 8 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 4 cm to 10 cm. Diameter: About 1.5 mm to 3 mm. Strength: Strong. Texture: Pubescent; attitude of hairs, outwardly to horizontal. Color: Close to 144B.

*Reproductive organs*.—Stamens: Quantity per flower: About 25 to 30. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruits: Quantity per truss: About seven to eight. Natural fruiting season: Relatively early and long fruiting season, plants develop fruit during the summer in The Netherlands, ripening time considered midseason; fruiting is non-remontant. Postharvest longevity: About ten days at 7° C. Length: About 2 cm to 4 cm. Diameter: About 3 cm to 6 cm. Shape: Primary fruits are relatively large and are round in shape; secondary fruits are smaller and conical to cone-shaped. Fruit cavity length: About 1.3 cm. Fruit cavity width: About 8 mm. Fruit weight per fruit, first quality: About 26.5 g. Fruit weight per plant, first quality: About 470 g. Firmness: Firm. Fragrance, taste: Pleasant; good balance between sweetness and acidity. Acidity: About 14.8 mmol $H_3O$/100 g. Sweetness: About 9.2 Brix. Luster: Uniformly glossy. Surface unevenness: Smooth. Color, surface: Close to 181A. Color, flesh: Close to 45A. Color, core: Close to 34A. Seed density: Medium. Achene position: Level with surface, slightly indented; width of band without achenes, relatively small. Achene weight: About 0.000667 g. Achene color: Close to 4A.

Disease and pest resistance: Plants of the new Strawberry have been observed to be moderately resistant to *Verticillium dahliae* and *Phytophthora cactorum*. Plants of the new Strawberry have not been observed to be resistant to pests and other pathogens common to Strawberry plants.

It is claimed:

1. A new and distinct Strawberry plant named 'Opera' as illustrated and described.

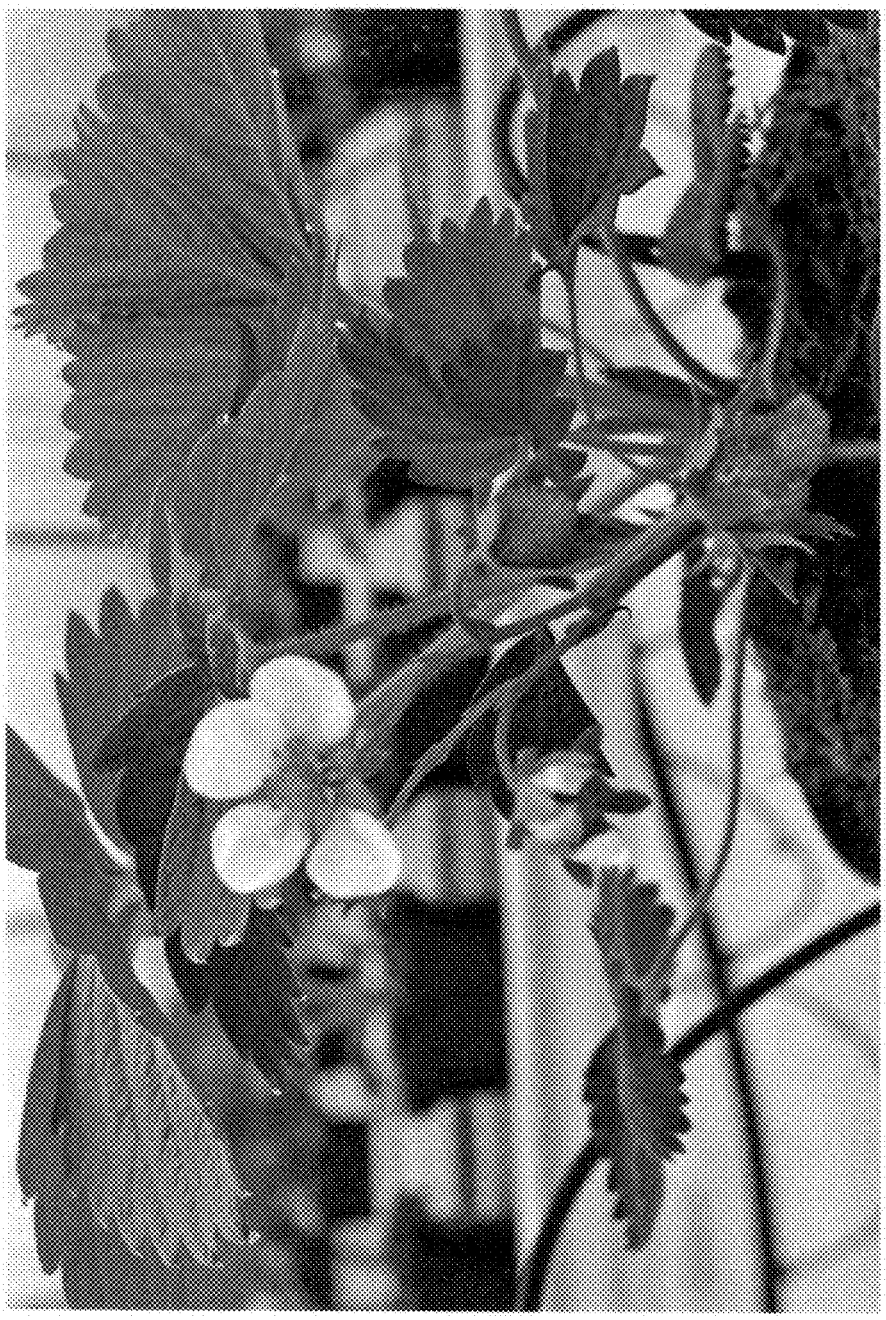

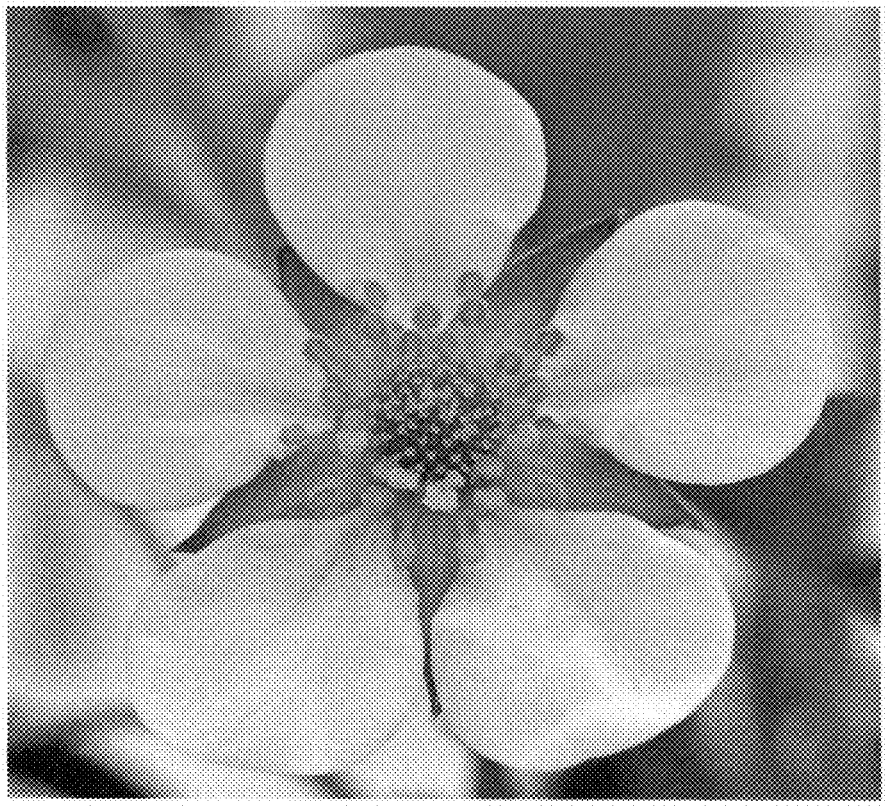

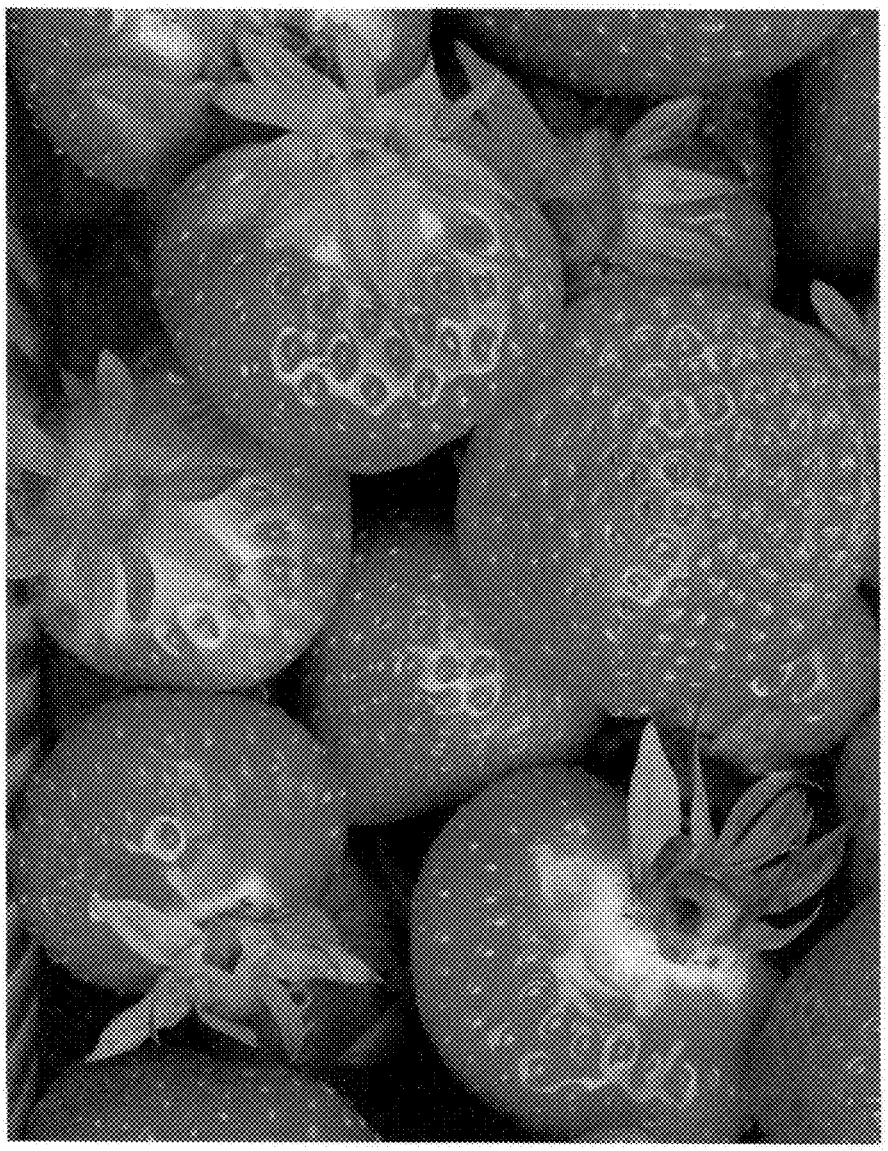

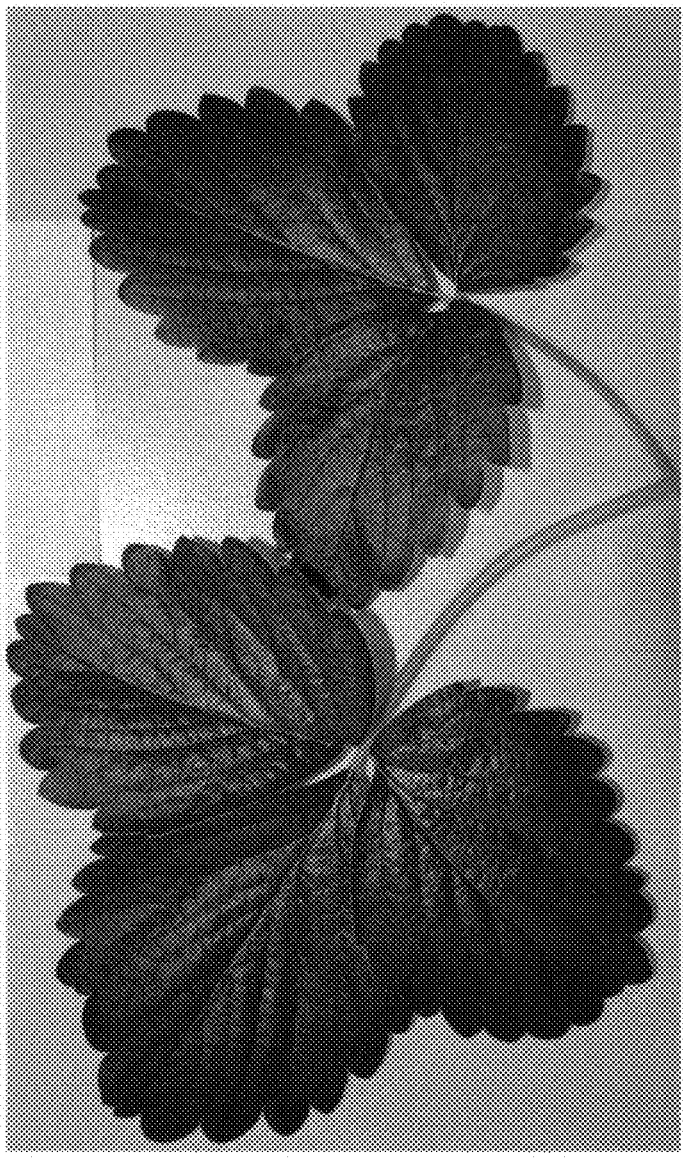

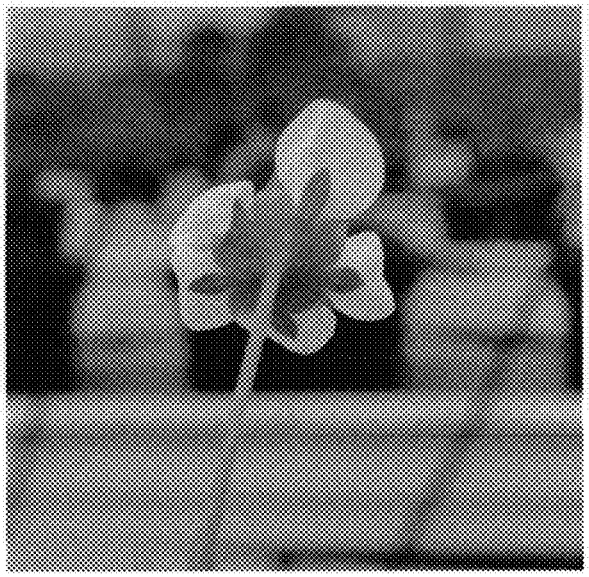

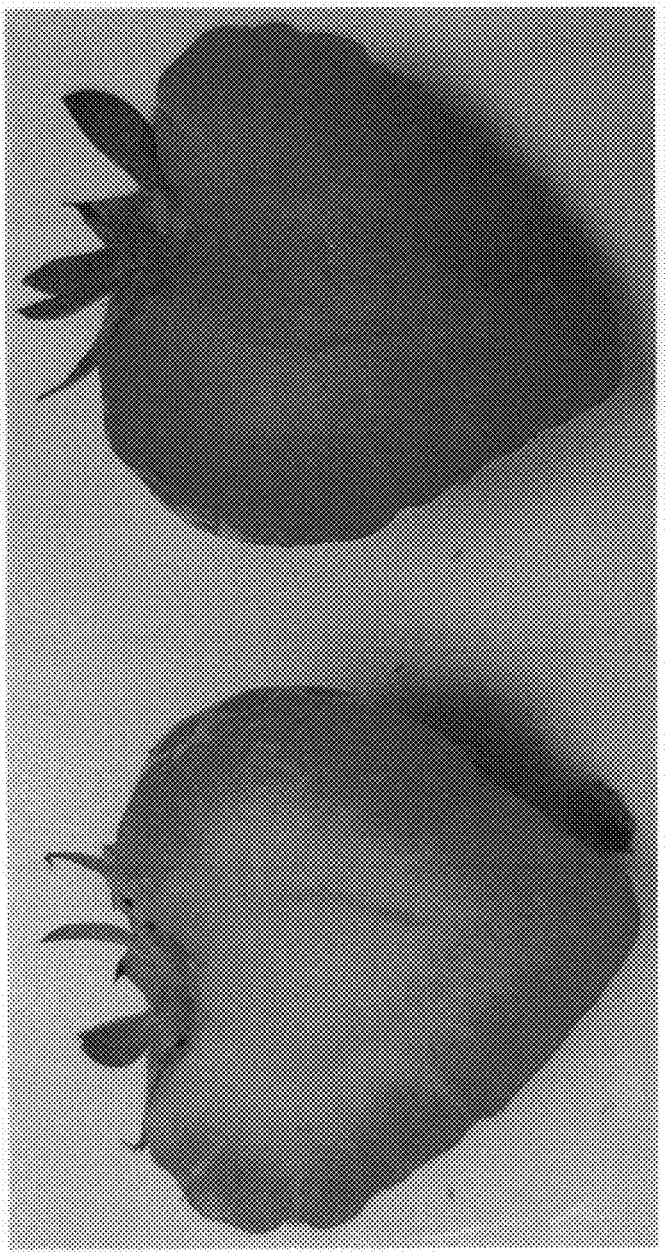

* * * * *